United States Patent
Haderlein et al.

(10) Patent No.: US 7,498,451 B2
(45) Date of Patent: Mar. 3, 2009

(54) OBTAINING AN ALIPHATIC DIALDEHYDE MONOACETAL

(75) Inventors: Gerd Haderlein, Grünstadt (DE); Hans-Georg Göbbel, Kallstadt (DE); Wolfgang Siegel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 547 days.

(21) Appl. No.: 10/536,900

(22) PCT Filed: Nov. 27, 2003

(86) PCT No.: PCT/EP03/13370

§ 371 (c)(1), (2), (4) Date: May 27, 2005

(87) PCT Pub. No.: WO2004/048359

PCT Pub. Date: Jun. 10, 2004

(65) Prior Publication Data
US 2006/0058538 A1    Mar. 16, 2006

(30) Foreign Application Priority Data
Nov. 28, 2002   (DE) ............................... 102 55 647

(51) Int. Cl.
*C07D 317/26* (2006.01)
*C07C 45/64* (2006.01)

(52) U.S. Cl. ...................... 549/454; 549/347; 549/375; 568/465

(58) Field of Classification Search .............. 549/484, 549/454, 347, 375; 568/465
See application file for complete search history.

(56) References Cited

U.S. PATENT DOCUMENTS 6,166,225 A    12/2000   Tanaka et al.

FOREIGN PATENT DOCUMENTS

| EP | 0987261 | 3/2000 |
|---|---|---|
| JP | 48039416 | 6/1973 |
| JP | 4861477 | 8/1973 |
| JP | 11-228566 | 8/1999 |

OTHER PUBLICATIONS

Botteghi, C. et al., Malonaldehyde, Succinaldehyde and Glutaraldehyde Monoacetals: Syntheses and Applications, Synthesis, 1985, p. 592-604.

*Primary Examiner*—Bernard Dentz
(74) *Attorney, Agent, or Firm*—Connolly Bove Lodge & Hutz LLP

(57) ABSTRACT

The invention relates to a process for obtaining a pure aliphatic dialdehyde monoacetal by reaction of the corresponding aliphatic dialdehyde or a precursor of the corresponding aliphatic dialdehyde with one or more aliphatic mono- or polyhydric alcohols while distillatively removing water to obtain a reaction mixture which is separated distillatively, which comprises carrying out the distillative separation continuously in a dividing wall column to obtain pure aliphatic dialdehyde monoacetal as a sidestream from the dividing wall column, or in two distillation columns to obtain crude aliphatic dialdehyde monoacetal as a sidestream in the first distillation column, feed the crude aliphatic dialdehyde monoacetal to the second distillation column and obtain pure aliphatic dialdehyde monoacetal as the sidestream from the second distillation column.

22 Claims, 3 Drawing Sheets

OBTAINING AN ALIPHATIC DIALDEHYDE MONOACETAL

CROSS REFERENCE TO RELATED APPLICATION

The present application is a National Stage application of PCT/EP2003/013370, filed Nov. 27, 2003, which claims priority from German Patent Application No. DE 102 55 674.4, filed Nov. 28, 2002.

The invention relates to a process for obtaining a pure aliphatic dialdehyde monoacetal.

Dialdehydes are valuable synthetic building blocks in organic synthesis, in particular of pharmaceuticals, agrochemicals and also other active and effective ingredients, as a consequence of the reactivity and the variety of reaction possibilities of the aldehyde functions. Particular interest attaches to dialdehydes in which one of the two aldehyde functions is masked, i.e. protected. It is thus possible in the synthetic sequence to selectively and protectively react both functional groups by suitable reactions in each case.

A particularly simple, at the same time effective and also easily detachable protecting group is the aldehyde acetal. Therefore, aliphatic dialdehydes in which one of the two aldehyde functions has been acetalized with alcohols or thiols, i.e. dialdehyde monoacetals and also their substitution products, in particular constitute interesting and valuable intermediates in organic synthesis.

The review article of C. Botteghi and F. Soccolini in Synthesis 1985, pages 592 to 604 discloses various synthetic possibilities for dialdehyde monoacetals of the general formula

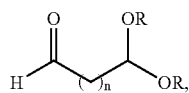

where n=1, 2 or 3.

However, the synthetic routes described are unsuitable for industrial scale use.

According to the current state of the art, especially for the particularly interesting monoacetals of glutaraldehyde, i.e. compounds corresponding to the above general formula where n=3, the only economic synthetic route on the industrial scale is the direct reaction of glutaraldehyde with the corresponding alcohol.

To this end, the following variants in particular are known:

In the process of JP 48-39416, glutaraldehyde is reacted directly under acid catalysis with ethylene glycol in a 2:1 ratio. The process affords the product of value, the monoethylene glycol acetal of glutaraldehyde, 2-(3-formylpropyl)-1,3-dioxolane (abbreviated to FPDO hereinbelow), in a 40% yield after distillation. However, the excess of glutaraldehyde has to be distillatively removed.

In the process of JP 48-61477, glutaraldehyde is reacted with an excess of ethylene glycol to give the diacetal. This is then hydrolyzed to give the monoacetal after isolation with water. After extractive purification, the product of value FPDO is obtained in a 48% yield.

In the process of JP 11-228566, glutaraldehyde is initially reacted with ethylene glycol, likewise to give the diacetal. However, this then disproportionates with further glutaraldehyde after isolation to give the product of value FPDO.

The existing processes have in particular the following disadvantages: In all reactions, a mixture of reactant, the monoacetal product of value and bisacetal is formed. In the process of JP 48-61477 or JP 11-228566 in which the bisacetal is deliberately prepared initially, the equilibrium with regard to the products is more advantageous. However, as before, the mixture has to be separated; additionally, an additional process stage is required.

One problem of all existing processes which has not yet been solved in an industrially and economically viable manner is that, as a consequence of the high reactivity of the two aldehyde functions in the dialdehyde reaction which is partially masked in the dialdehyde monoacetal product, the reaction mixtures, in particular at elevated temperature, readily polymerize. This delivers highly viscous products which are difficult to handle and lead to yield losses. Especially in the case of distillative workup as a batch distillation with high residence times at high temperature, as carried out in the above-described processes, this leads to product losses.

DETAILED DESCRIPTION OF THE INVENTION

It is an object of the invention to provide a process which leads in an economically advantageous manner in one stage to the dialdehyde monoacetal product of value in a high degree of purity of at least 98% by weight, in order to fulfill the specification requirements for use in subsequent syntheses, and in which the product losses by polymerization are kept low. Especially in the distillation of the crude material, product losses should be minimized.

We have found that this object is achieved by a process for obtaining a pure aliphatic dialdehyde monoacetal by reaction of the corresponding aliphatic dialdehyde or a precursor of the corresponding aliphatic dialdehyde with one or more aliphatic mono- or polyhydric alcohols while distillatively removing water to obtain a reaction mixture which is separated distillatively, which comprises carrying out the distillative separation continuously in a dividing wall column to obtain pure aliphatic dialdehyde monoacetal as a sidestream from the dividing wall column, or in two distillation columns to obtain crude aliphatic dialdehyde monoacetal as a sidestream in the first distillation column, feed the crude aliphatic dialdehyde monoacetal to the second distillation column and obtain pure aliphatic dialdehyde monoacetal as the sidestream from the second distillation column.

In the present context, the crude aliphatic dialdehyde monoacetal is a mixture which is formed of at least 90% by weight, preferably of at least 97% by weight, of the product of value, the aliphatic dialdehyde monoacetal.

In the present context, the pure aliphatic dialdehyde monoacetal is a mixture which is formed of at least 98% by weight, preferably of at least 99% by weight, of the product of value, the aliphatic dialdehyde monoacetal.

The invention is not restricted with regard to the specific performance of the reaction of the aliphatic dialdehyde or of a precursor of the aliphatic dialdehyde with one or more aliphatic, mono- or polyhydric alcohols.

In a preferred variant, the dialdehyde, preferably glutaraldehyde, is initially charged in aqueous solution, preferably up to 50% by weight in water, and preheated to from 30 to 80° C., preferably from 40 to 50° C., more preferably to 45° C. Subsequently, reduced pressure is applied so that the water of solution distills off. At the same time as the water is distilled off, alcohol or a mixture of alcohols, preferably ethylene glycol, is added. Toward the end of the reaction, the temperature is increased to from 50 to 110° C., preferably from 80 to 90° C., more preferably to 85° C.

In a further process variant, the aliphatic dialdehyde, preferably glutaraldehyde, which is present as an aqueous solution, is dewatered by applying reduced pressure, preferably at slightly elevated temperature, in the range from 30 to 80° C., preferably from 40 to 50° C., more preferably at 45° C. However, as a consequence of the tendency to spontaneous polymerization, care has to be taken that the dewatered dialdehyde is kept at a temperature within the abovementioned range and also constantly in motion, and is reacted immediately after the dewatering. To this end, in a similar manner to the process variant, the alcohol or the mixture of alcohols, preferably ethylene glycol, is added.

In a further process variant, it is possible to initially charge both reactants, the dialdehyde and also the alcohol or alcohols and optionally the catalyst, preferably using the dialdehyde in aqueous solution and subsequently distilling off both the water of solution and the water of reaction. However, the space-time yield in this process variant is worsened compared to the above-described variants.

The aliphatic dialdehyde used is preferably a substance from the following list: malonaldehyde, succinaldehyde, glutaraldehyde or adipaldehyde or their alkyl-substituted derivatives, more preferably glutaraldehyde, in particular in aqueous solution, preferably in 50% aqueous solution, or its precursor 2-hydroxy-3,4-dihydo-2H-pyran.

The alcohol component used may in particular be a monohydric alcohol such as methanol, ethanol, n-propanol, i-propanol, n-butanol, sec-butanol, i-butanol, or a diol, in particular ethylene glycol, 1,2-propylene glycol, 1,3-propylene glycol, 1,2-butanediol, 1,3-butanediol or 1,4-butanediol, and particular preference is given to ethylene glycol.

Particular preference is given to using glutaraldehyde with ethylene glycol in a molar ratio in the range from 1:1.5 to 1.5:1, preferably from 1:1.2 to 1.2:1, in particular of 1.0:1.0. Although the conversion to the aliphatic dialdehyde monoacetal also proceeds uncatalyzed, preference is given to using an acidic catalyst, in particular a cation exchanger, a mineral acid, preferably sulfuric acid, hydrochloric acid, more preferably orthophosphoric acid or an organic acid, in particular acetic acid, p-toluenesulfonic acid or methanesulfonic acid, in a concentration of from 0.02 to 5% by weight, preferably from 0.1 to 1% by weight, more preferably of 0.3% by weight, based on the total weight of the reaction mixture.

The reaction mixture which has been virtually completely freed of the water burden by distillation is subsequently distillatively separated to obtain the product of value, the aliphatic dialdehyde monoacetal.

The inventors have recognised that it is essential for this purpose to carry out the distillation continuously. Compared to the existing distillations carried out batchwise, continuous distillations have the advantage of a shorter residence time of the liquid phase product and therefore lower thermal stress and damage. By carrying out the distillation continuously in accordance with the invention, a significant improvement in the distillation yield is achieved.

The continuous distillative separation can be carried out in two successive distillation columns or, particularly advantageously, in a dividing wall column.

To perform the distillation in two successive distillation columns, the virtually anhydrous reaction mixture is firstly fed to a first distillation column which advantageously has from 40 to 80 theoretical plates, preferably from 50 to 70 theoretical plates, more preferably from 60 to 70 theoretical plates, and continuously distilled at a top pressure of from 5 to 500 mbar, preferably from 10 to 300 mbar, more preferably from 15 to 100 mbar.

Unconverted glutaraldehyde is removed as the top product and preferably recycled into the synthesis. Crude aliphatic dialdehyde monoacetal, i.e. a mixture which contains at least 90% by weight, preferably at least 97% by weight, of the monoacetal product of value, is removed from the rectifying section of the column, i.e. above the feed of the mixture to be separated.

At the bottom of the column, the diacetal and also more highly condensed products are obtained. Suitable bottom evaporators are in particular falling-film evaporators, since they guarantee gentle evaporation and thus do not stress the thermally sensitive product.

Preference is given to separating the bottom effluent of the first distillation column in a downstream thin film evaporator into two streams at a pressure of preferably about 10 mbar: the volatile diacetal is removed overhead, condensed and recycled to the acetalization stage for dissociation. The high-boiling polymers are utilized thermally.

The crude aliphatic dialdehyde monoacetal is subsequently fed to a second distillation column which preferably has from 30 to 70 theoretical plates, in particular from 40 to 70 theoretical plates, more preferably from 50 to 70 theoretical plates, and is operated at a top pressure of from 5 to 500 mbar, preferably from 10 to 300 mbar, more preferably from 15 to 100 mbar.

Remaining dialdehyde is removed from the second distillation column as a top stream and preferably recycled into the synthesis.

Pure aliphatic dialdehyde monoacetal, i.e. a mixture which contains at least 98% by weight of the dialdehyde monoacetal product of value, preferably 99% by weight of the product of value, is removed as a vaporous sidestream from the stripping section of the column, i.e. below the feed of the mixture to be separated into the second distillation column.

At the bottom of the column, higher-boiling components are obtained which still contain fractions of the aliphatic dialdehyde monoacetal product of value. In order to reduce loss of product of value, preference is given to recycling the bottom stream into the first distillation column.

In a particularly advantageous process variant, the continuous distillation is carried out in a single apparatus, a dividing wall column.

It is known that dividing wall columns enable a particularly economical separation, which is advantageous especially with regard to the capital and energy costs, of multicomponent mixtures to obtain one or more pure sidestreams. In sections of a dividing wall column, transverse mixing of the liquid and vapor streams is prevented by dividing wall, generally a metal sheet disposed in the longitudinal direction of the column. Customarily, the dividing wall divides the column interior into a feed section, a takeoff section, an upper combined column region and also a lower combined column region. Between the feed region and the takeoff region is disposed the dividing wall which prevents transverse mixing of liquid and vapor streams over the entire column cross section in these column regions. This makes it possible to obtain a product in pure form at a sidestream takeoff. The dividing wall may be welded fast or else only inserted loosely, the latter variant having the advantage of low capital costs.

To perform the distillative separation of the reaction mixture in the present process in a dividing wall column, the virtually anhydrous reaction mixture is fed to a dividing wall column which has a liquid sidestream and preferably from 40 to 100 theoretical plates, in particular from 50 to 90 theoretical plates, more preferably from 60 to 85 theoretical plates, and is operated at a top pressure of from 5 to 500 mbar, preferably from 10 to 300 mbar, more preferably from 15 to 100 mbar. In the dividing wall column, the reaction mixture is continuously separated distillatively into three fractions: into a low boiler fraction which contains unconverted reactants and which is preferably recycled into the reaction stage, into a medium boiler fraction which contains the pure dialdehyde monoacetal, i.e. a mixture having a product of value of at least 98% by weight, preferably at least 99% by weight, and also a high boiler fraction which contains the diacetal and also higher-boiling components.

Particularly suitable bottom evaporators for the dividing wall column are falling-film evaporators, since they ensure gentle evaporation and do not stress the thermally sensitive product.

With regard to the separating internals, there is in principle no restriction, i.e. it is possible to use trays, random packings or structured packings, for example sheet metal or fabric packings, preferably having specific surface areas of from 250 to 750 $m^2/m^3$. Particular preference is given to fabric packings as a consequence of their relatively low pressure drop per plate, and also their better separating performance in vacuum distillations, as used in the present context.

The bottom effluent of the dividing wall column is subsequently preferably fed to a thin-film evaporator and separated there, preferably at a pressure of about 10 mbar, into two streams: the volatile diacetal is removed in vaporous form, condensed and recycled into the acetalization stage for dissociation. The high-boiling polymers are utilized thermally.

The dividing wall column is preferably divided in such a way that all column regions, i.e. the upper combined column region, the rectifying section of the feed region, the stripping section of the feed region, the rectifying section of the takeoff region, the stripping section of the takeoff region and also the lower combined column region each have 5 to 50%, preferably from 15 to 30%, of the total number of theoretical plates of the dividing wall column.

Preference is further given to the dividing wall column being designed in such a way that the sum of the number of theoretical plates of the two parts of the feed region, i.e. the rectifying section and the stripping section, is from 80 to 110%, preferably from 90 to 100%, of the sum of the number of theoretical plates of the two parts (rectifying section and stripping section) of the takeoff region.

Feed and sidestream takeoff can be disposed at different heights in the dividing wall column, and the feed is disposed preferably from 1 to 8 theoretical plates, more preferably from 3 to 5 theoretical plates, higher or lower than the sidestream takeoff.

The division ratio of the liquid at the upper end of the dividing wall is preferably adjusted in such a way that the concentration of those components of the high boiler fraction for which a certain limiting value in the sidestream is predefined in the liquid at the upper end of the dividing wall is from 10 to 80%, preferably from 30 to 50%, of the value which is predefined for the sidestream product. At a higher content of high boilers, the liquid division is adjusted in such a way that more liquid is conducted to the feed region, while, at a lower concentration of high boilers, less liquid is conducted to the feed region.

The heating output in the bottom evaporator is preferably adjusted in such a way that the concentration of those components of the low boiler fraction for which a certain limiting value in the sidestream is predefined at the lower end of the dividing wall is adjusted in such a way that it is from 10 to 80%, preferably from 30 to 50%, of the value which is predefined for the sidestream product. At a higher content of components of the low boiler fraction, the heating output is increased, and at a lower content, it is reduced.

The distillate is removed under temperature control, and the control temperature used is a measuring point in the upper combined column region, which is disposed from 3 to 8, preferably from 4 to 6, theoretical plates below the upper end of the column.

The bottom product is likewise removed under temperature control. The control temperature is a measuring point in the lower combined column region which is disposed from 3 to 8, preferably from 4 to 6, theoretical plates above the lower end of the column.

The side product is preferably withdrawn under level control, and the liquid level in the bottom evaporator serves as the control parameter.

A cost comparison between the two variants of the distillative separation in two distillation columns connected in series on the one hand and in a dividing wall column on the other hand shows that the dividing wall column is about 30% cheaper both with regard to the capital costs and the energy costs. A further advantage of separation in a dividing wall column is the distinct reduction in the thermal stress on the sensitive product, which results from the shortening of the residence time in the bottom evaporator, especially as a consequence of the reduction to a single bottom evaporator.

In a particularly advantageous process variant, the substantially anhydrous reaction mixture is heated to from 80 to 130° C. before it is fed to distillative separation.

It has been found that, surprisingly, the viscosity of the reaction mixture can be significantly reduced by heating, especially into a range within which it can be readily transported by pumps. In addition, the heating achieves a significant rise in product of value, the aliphatic dialdehyde monoacetal, in the reaction mixture.

According to the invention, the heating is effected at temperatures in the range from 80 to 130° C., preferably from 90 to 110° C. The heating time is uncritical: a minimum duration of 15 minutes may be sufficient, and an upper limit is not decisive for the success of the invention, but rather at most conceivable on the basis of economic considerations. Preference is given to heating for from 30 minutes to 4 hours, more preferably for 1 hour.

The pressure at which heating is effected is not critical: Heating may be effected under reduced pressure, under increased pressure or at atmospheric pressure, but preferably at atmospheric pressure.

In a further particularly advantageous process variant, the distillative separation of the optionally heated reaction mixture is carried out with the addition of a high-boiling diluent into the lower region of the first distillation column or into the lower combined column region of the dividing wall column.

The high-boiling diluent has to be miscible with the reaction mixture, it must not react with the reaction mixture and should have a lower vapor pressure than any individual component of the reaction mixture and also than the reaction mixture. Preference is given to adding the high-boiling diluents in a proportion of from 1 to 30% by weight, preferably from 2 to 20% by weight, more preferably from 5 to 15% by weight, based on the mixture to be separated distillatively.

A particularly suitable diluent is a substance or a mixture of substances selected from the following listed groups: alkanes, aromatics or polyethers, preferably polypropylene glycols or polyethylene glycols, more preferably polyethylene glycol having an average molecular mass of 300.

The addition of the high-boiling diluent prevents caking and polymerization of the distillation bottoms to the heat exchange surfaces, and thus improves the yields of product of value.

The invention is illustrated by the examples which follow and also a drawing.

EXAMPLES 1 TO 3

Reaction of glutaraldehyde with ethylene glycol to give 2-(3-formylpropyl)-1,3-dioxolane (FPDO)

Example 1

Simultaneous Distilling Off of Water of Solution and Addition of Ethylene glycol A 1 l stirred apparatus with an attached 10 cm randomly packed column of Raschig rings and a distillation head with condenser was initially charged with 800 g of a glutaraldehyde solution (50% in water). At an internal temperature of from 60 to 65° C. and a vacuum of 200 mbar, the water was distilled off. As soon as the first distillate had been obtained, a solution of 1.2 g of orthophosphoric acid (99%) in 248 g of ethylene glycol was added dropwise within two hours at the same time as the water was distilled off. The reaction mixture was conducted at 65° C./200 mbar for a further hour after the addition. Afterwards, the vacuum was improved stepwise to 25 mbar, the internal temperature was increased to 85° C. and all of the water was distilled off. 530 g of a very viscous, colorless crude solution were obtained. Composition (GC area %): 50.5% of FPDO, 36.9% of 1,3-bis(1,3-dioxolan-2-yl)propane (bisacetal), 9.0% of glutaraldehyde.

Example 2

Distilling Off Water of Solution Followed by Addition of Ethylene Glycol

A 2 l stirred apparatus having an attached 10 cm randomly packed column of Raschig rings and a distillation head with condenser was initially charged with 1200 g of a glutaraldehyde solution (50% in water) and afterwards the water was distilled off at an internal temperature of from 70 to 80° C. and a vacuum of 150 mbar. Subsequently, a solution of 2 g of orthophosphoric acid (99%) in 372 g of ethylene glycol was added dropwise at an internal temperature of from 75 to 83° C. within 90 minutes and the reaction mixture was subsequently stirred for a further 90 minutes. Afterwards, vacuum was applied which was improved stepwise from 100 to 50 mbar to distill off the water of reaction at an internal temperature of from 70 to 88° C. 850 g of a very viscous, colorless crude solution was obtained. Composition (GC area %): 50.7% of FPDO, 25.0% of 1,3-bsis(1,3-dioxolan-2-yl)propane (bisacetal), 12.7% of glutaraldehyde, 3.0% of ethylene glycol.

Example 3

Distilling Off Water of Solution and Water of Reaction

A 1 l stirred apparatus with an attached 10 cm randomly packed column of Raschig rings and a distillation head with condenser was initially charged with 800 g of a glutaraldehyde solution (50% in water), 248 g of ethylene glycol and 1.2 g of orthophosphoric acid (99%). The reaction mixture was stirred at 60° C. for 45 minutes. Afterwards, water was distilled off at 180 mbar within 3 hours. Subsequently, the vacuum was improved stepwise to 30 mbar and the internal temperature increased to 90° C., in order to distill off all of the water. 568 g of a very viscous, slightly cloudy crude solution were obtained. Composition (GC area %): 56.4% of FPDO, 19.5% of 1,3-bis(1,3-dioxolan-2-yl)propane (bisacetal), 14.8% of glutaraldehyde, 2.2% of ethylene glycol.

Comparative Example

Heating

A crude solution prepared according to example 1 having an FPDO content determined by gas chromatography with an internal standard of 50% by weight was heated at 60° C. and atmospheric pressure under protective gas. The FPDO content fell to 36% by weight of FPDO after heating for 24 hours and to 29.4% by weight of FPDO after heating for 72 hours.

Example 4

Heating

Various samples of a crude solution prepared according to example 1 which had been stored at 60° C. for a short time and whose FPDO content determined by gas chromatography with an internal standard was 35.3% by weight were heated with variation of temperature and time. The FPDO (product of value) content and also the kinematic viscosities to DIN 51562 were determined for the heated solutions.

The results are listed in the table 1 below:

|  | Temperature | Time [h] | % by weight of FPDO |
| --- | --- | --- | --- |
| 4.0 |  | 0 | 35.3 |
| 4.1 | 90° C. | 1 | 40.0 |
| 4.2 |  | 3 | 41.4 |
| 4.3 |  | 5 | 41.7 |
| 4.4 | 100° C. | 1 | 43.4 |
| 4.5 |  | 3 | 43.2 |
| 4.6 |  | 5 | 41.7 |
| 4.7 | 110° C. | 1.5 | 45.6 |
| 4.8 |  | 3 | 46.6 |
| 4.9 | 120° C. | 1.5 | 47.5 |
| 4.10 |  | 3 | 46.0 |

The kinematic viscosity of the crude solution of comparative example 4.0, i.e. the unheated sample, was 6040 mm$^2$/s at 20° C., whereas the viscosity of sample 4.8 (heated at 110° C. for 3 hours) was only 17.5 mm$^2$/s at 20° C. The heating therefore leads to a significant reduction in viscosity. In addition, the FPDO (product of value) content clearly increases, as can be seen in the last column of the above table.

Comparative Example

Distillation 750 g of a crude solution prepared according to example 2 and having an FPDO content of 50% by weight were distilled batchwise in a 60 cm randomly packed column of Raschig rings at a bottom temperature of 150° C., a vacuum of 1.5 mbar and a residence time in the bottom of about 10 hours. In total, only 230 g of FPDO could be removed distillatively, which corresponds to a distillation yield of only 60%. The bottoms were extremely viscous and polymerized solids which had formed had blocked the lower column region.

Example 5

Simulation of the Thermal Stress on the Mixture in a Column without addition of high-boiling diluent To simulate the thermal stress on the crude solution in the distillation in a column equipped with a falling-film circulation evaporator, 500 g of a crude solution prepared according to example 1 and heated at 95° C. for 2 hours was continuously distilled at a feed rate of 500 g/h and a residence time of approx. 1 minute at a temperature of from 150 to 155° C. and a vacuum to 2 mbar. After half of the feed, significant black deposits could be observed and the bottom outlet became blocked by polymer, so that the experiment had to be terminated.

Example 6

Simulation of the Thermal Stress on the Mixture in a Column with the addition of high-boiling diluents To simulate the thermal stress on the crude solution in the distillation in a column equipped with a falling-film circulation evaporator, 3700 g of crude material prepared according to example 1 and heated at 95° C. for 2 hours, except in a mixture with 10% by weight of polyethylene glycol of molar mass 300, was continuously distilled on a thin-film evaporator at a temperature of 135° C. and a vacuum of 1 mbar. The feed rate, as in example 5, was 500 g/h and the residence time about 1 minute. The experiment was terminated after 7 hours, without any deposit having been observed on the apparatus. 996 g of distillate and 1670 g of bottom effluent were obtained.

Example 7

Distillation without Addition of High-Boiling Diluents

In a column (diameter 300 mm, Sulzer structured packing, 60 theoretical plates), 10 t of crude material prepared in a similar manner to example 1 and having an FPDO content of 40% by weight were continuously distilled in two stages. In the first stage (20 mbar; residence time: approx. 4 h), the monoacetal, FPDO, was initially obtained in a purity of approx. 95% in the liquid sidestream. In a second stage (15 mbar), the pure FPDO product was then likewise obtained in a vaporous sidestream. Unconverted glutaraldehyde and ethylene glycol were each obtained overhead; the bisacetal was obtained via the bottom of the first distillation stage and was recycled back into the synthesis. 3.8 t of FPDO in a purity of >99% were obtained. The distillation yield was 95%.

BRIEF DESCRIPTION OF THE DRAWINGS

FIG. 1 shows a first distillation column K1 to which the anhydrous reaction mixture (stream A) is fed in the middle region. The distillation column K1 is equipped with a bottom evaporator and also a condenser at the top of the column. The top stream is condensed in the condenser at the top of the column, partly removed as stream B1 which contains predominantly glutaraldehyde and the remainder is fed back to the column as reflux. Crude FPDO (stream C1) is removed as a liquid sidestream from the rectifying section of the column. The bottom stream D is divided into two streams in a thin-film evaporator V, a top stream containing the volatile diacetal which is partly recycled to the synthesis as stream E and a bottom stream comprising high boilers which is discharged.

The crude FPDO (stream C1) is fed to the second distillation column K2 in the middle region thereof. The column K2 is likewise equipped with a condenser at the top of the column and also with a bottom evaporator. The top stream of column K2 is condensed in the condenser at the top of the column, partly removed as stream B2 which consists predominantly of glutaraldehyde, and the remainder is fed back to the column as reflux. A pure FPDO-containing stream (stream C2) is removed in vaporous form from the stripping section of column K2 and condensed. The bottom stream is recycled into column K1.

Figure 1:
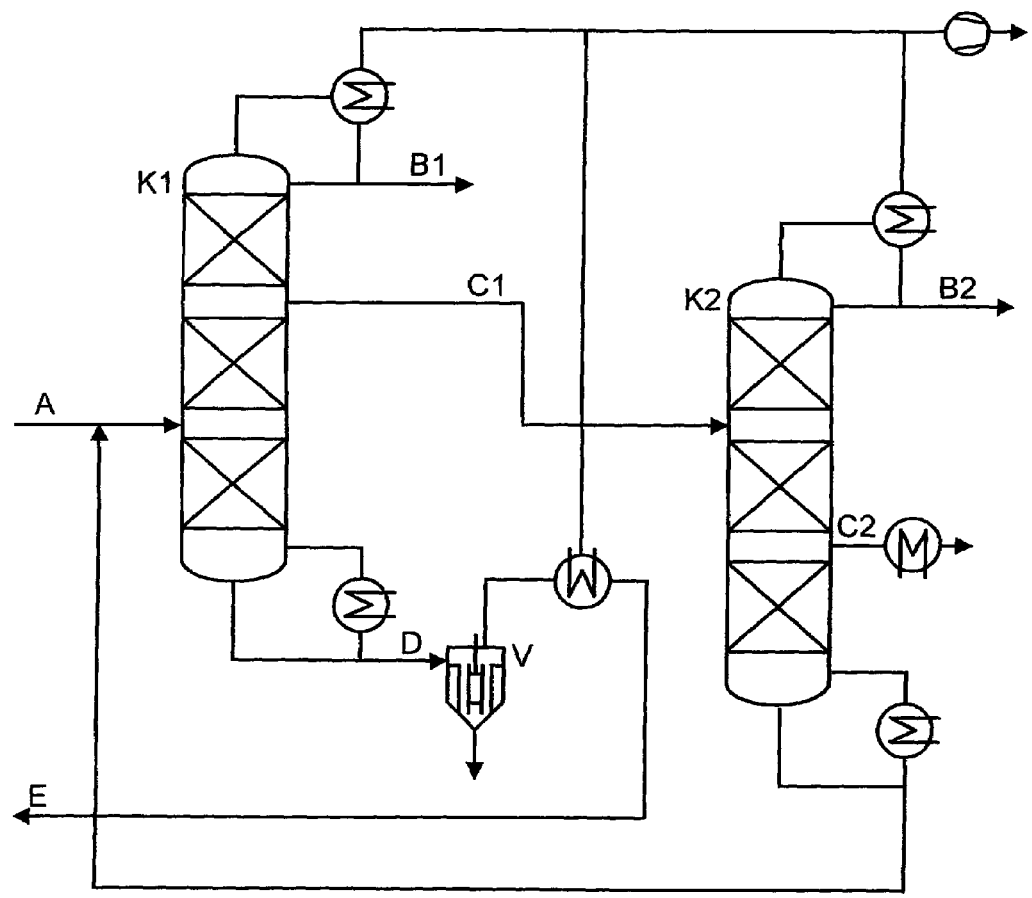
FIG. 1 shows a distillation scheme having two distillation columns connected in series.
Figure 2:
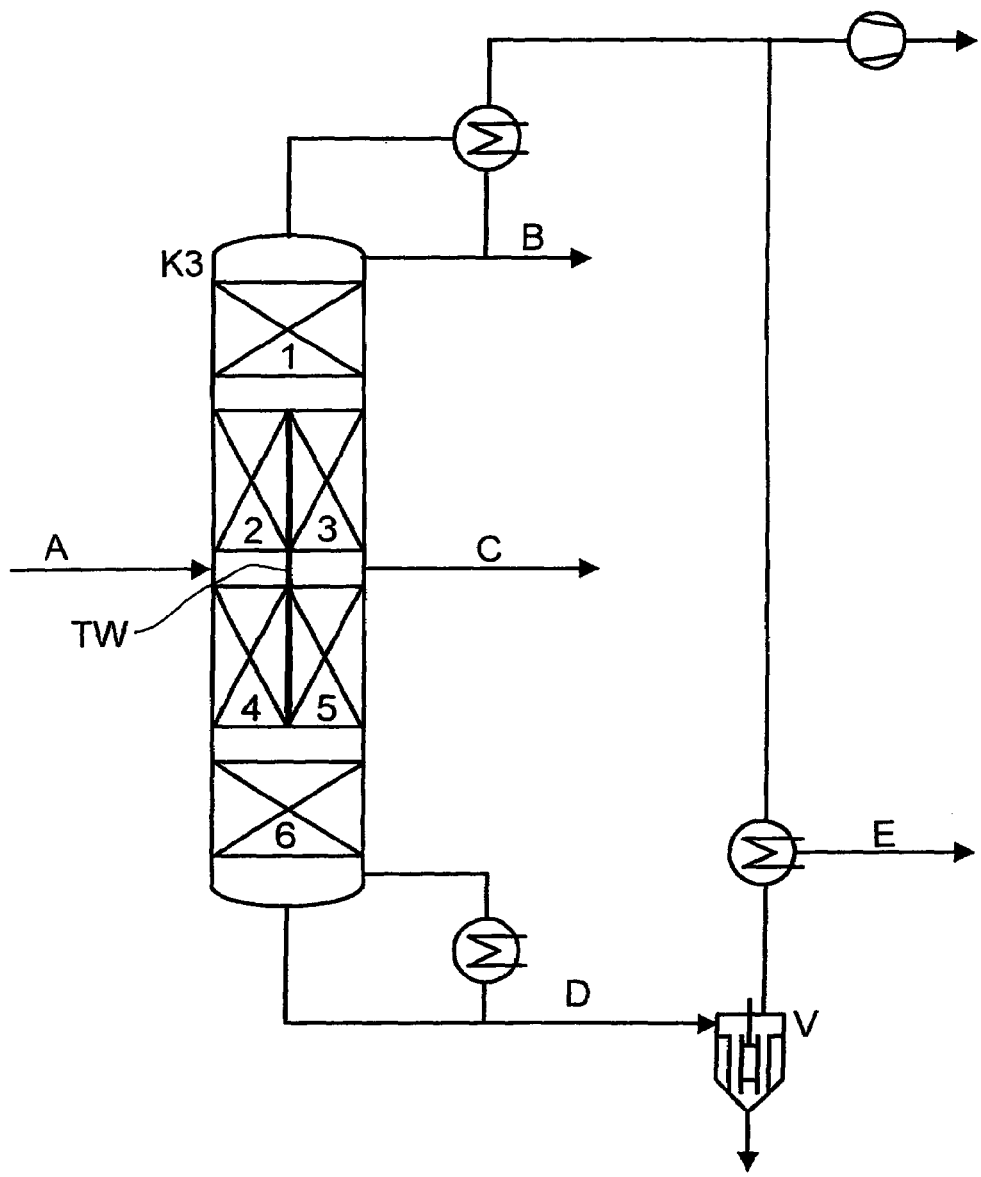
FIG. 2 shows a distillation scheme having a dividing wall column and
FIG. 3 shows a distillation scheme having a dividing wall column with the inclusion of the control apparatus.

FIG. 2 shows a dividing wall column K3 having a dividing wall TW disposed in the longitudinal direction of the column and separating the column interior into a feed region having a rectifying section 2 and stripping section 4, and also into a takeoff region having a rectifying section 3 and stripping section 5, and also into an upper combined column region 1 and a lower combined column region 6. The anhydrous reaction mixture is fed to the dividing wall column as stream A into the middle region of the feed region, the top stream is condensed in a condenser at the top of the column, partly removed as stream B comprising predominantly glutaraldehyde and the remainder is fed back to the column as a reflux stream. FPDO (stream C) is removed from the takeoff region of the column. The bottom stream D is separated in a thin-film evaporator V into a top stream comprising predominantly the diacetal which is recycled into the synthesis as stream I and also into a bottom stream which is discharged.

Figure 3:
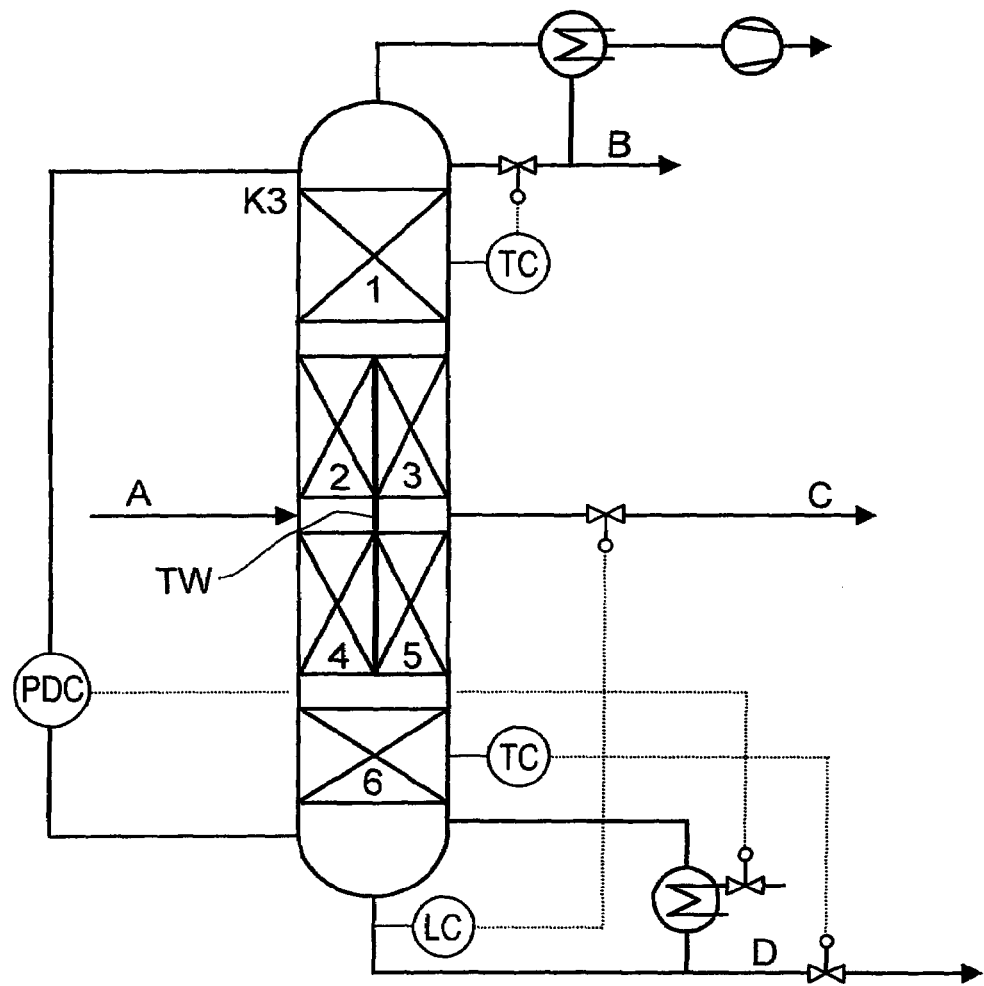

The schematic representation in FIG. 3 illustrates the control apparatus for the dividing wall column K3. TC indicates temperature controllers, LC is a liquid level controller and PDC is a differential pressure meter.

We claim:

1. A process for obtaining a pure aliphatic dialdehyde monoacetal comprising a reaction of the corresponding aliphatic dialdehyde or a precursor of the corresponding aliphatic dialdehyde with one or more aliphatic mono- or polyhydric alcohols while distillatively removing water to obtain a reaction mixture which is separated distillatively, said process further comprising carrying out the distillative separation continuously in (i) a dividing wall column to obtain pure aliphatic dialdehyde monoacetal as a sidestream from the dividing wall column, or (ii) in two distillation columns to obtain crude aliphatic dialdehyde monoacetal as a sidestream in the first distillation column, feeding the crude aliphatic dialdehyde monoacetal to the second distillation column, and obtaining pure aliphatic dialdehyde monoacetal as the sidestream from the second distillation column.

2. A process as claimed in claim 1, wherein the reaction mixture is heated to from 80 to 130° C. before the distillative separation.

3. A process as claimed in claim 1, wherein the reaction mixture is heated for at least 15 minutes.

4. A process as claimed in claim 1, wherein the aliphatic dialdehyde is selected from the group consisting of malonaldehyde, succinaldehyde, glutaraldehyde, and adipaldehyde.

5. A process as claimed in claim 1, wherein the aliphatic dialdehyde is glutaraldehyde or its precursor, 2-hydroxy-3,4-dihydro-2H-pyran.

6. A process as claimed in claim 1, wherein the aliphatic mono- or polyhydric alcohol is a diol.

7. A process as claimed in claim 5, wherein glutaraldehyde is reacted with ethylene glycol in a molar ratio in the range from 1:1.5 to 1.5:1.

8. A process as claimed in claim 1, wherein the reaction is carried out in the presence of an acidic catalyst, in a concentration of from 0.02 to 5% by weight based on the total weight of the reaction mixture.

9. A process as claimed in claim 1, wherein the optionally heated reaction mixture is continuously separated in two distillation columns to remove the crude aliphatic dialdehyde monoacetal as a sidestream in a first distillation column and the pure aliphatic dialdehyde monoacetal as a sidestream in a second distillation column.

10. A process as claimed in claim 1, wherein the optionally heated reaction mixture is separated in a dividing wall column having a vertical dividing wall which is disposed in the longitudinal direction of the column and divides the column into a feed region, a takeoff region, a lower combined column region and also an upper combined column region, to recover pure aliphatic dialdehyde monoacetal as a sidestream from the withdrawal region.

11. A process as claimed in claim 1, wherein the distillative separation of the optionally heated reaction mixture is carried out with the addition of a high-boiling diluent in the lower region of the first distillation column or in the upper combined column region of the dividing wall column.

12. A process as claimed in claim 11, wherein the high-boiling diluent is a substance or a mixture of substances selected from the group consisting of: alkanes, aromatics or polyethers, preferably polypropylene glycols, and polyethylene glycols.

13. A process as claimed in claim 3, wherein the reaction mixture is heated from 30 minutes to 4 hours, at from 90 to 110° C.

14. A process as claimed in claim 13, wherein the reaction mixture is heated for 1 hour.

15. A process as claimed in claim 5, wherein the glutaraldehyde is used in aqueous solution.

16. A process as claimed in claim 15, wherein the aqueous solution of glutaraldehyde is a 50% by weight aqueous solution.

17. A process as claimed in claim 6, wherein the aliphatic diol is selected from the group consisting of ethylene glycol, 1,2-propylene glycol, 1,3-propylene glycol, 1,2-butanediol, 1,3-butanediol, and 1,4-butanediol.

18. A process as claimed in claim 17, wherein the aliphatic diol is ethylene glycol.

19. A process as claimed in claim 7, wherein glutaraldehyde is reacted with ethylene glycol in a molar ratio in the range from 1:1.2 to 1.2:1.

20. A process as claimed in claim 19, wherein glutaraldehyde is reacted with ethylene glycol in a molar ratio in the range from 1.0:1.0.

21. A process as claimed in claim 8, wherein the acidic catalyst is selected from the group consisting of a cation exchanger, a mineral acid, and an organic acid.

22. A process as claimed in claim 12, wherein the polyethylene glycol has an average molecular mass of 300.

\* \* \* \* \*